United States Patent [19]

Regnier et al.

[11] Patent Number: 5,026,701
[45] Date of Patent: Jun. 25, 1991

[54] MORPHOLINE COMPOUNDS, COMPOSITIONS AND USE

[75] Inventors: Gilbert Regnier, Chatenay Malabry; Claude Guillonneau, Clamart; Jean Lepagnol, Chatou; Pierre Lestage, Paris, all of France

[73] Assignee: Adir et Compagnie, Courbevoie, France

[21] Appl. No.: 603,522

[22] Filed: Oct. 25, 1990

[30] Foreign Application Priority Data

Nov. 6, 1989 [FR] France ................................ 89 14489

[51] Int. Cl.$^5$ .................. A61K 31/535; C07D 413/12
[52] U.S. Cl. ................................ 514/235.2; 544/128; 514/878; 514/879
[58] Field of Search ...................... 544/128; 514/235.2, 514/878, 879

[56] References Cited

U.S. PATENT DOCUMENTS 4,782,054 11/1988 Regnier et al. ...................... 544/128

Primary Examiner—Robert W. Ramsuer
Attorney, Agent, or Firm—Gordon W. Hueschen

[57] ABSTRACT

New morpholine compounds of the formula:

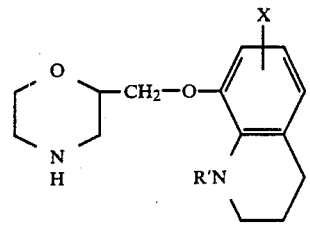

in which: X, bonded to the aromatic nucleus, represents halogen or trifluoromethyl and R' represents hydrogen, ($C_1$–$C_5$)alkyl optionally including a double bond, or aralkyl; in racemic and enantiomeric forms, and physiologically tolerable acid addition salts thereof.

These compounds and their physiologically tolerable salts can be used therapeutically especially in the treatment of ischaemic syndromes and cerebral ageing.

10 Claims, No Drawings

MORPHOLINE COMPOUNDS, COMPOSITIONS AND USE

The present invention provides morpholine compounds of the general formula I:

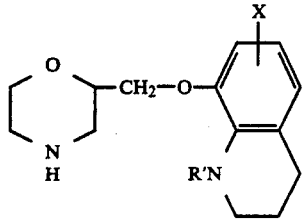

in which
X, bonded to the aromatic nucleus, is selected from the group consisting of:
halogen atoms such as fluorine and chlorine atoms, and
a trifluoromethyl radical; and
R' is selected from the group consisting of:
a hydrogen atom,
straight-chain or branched alkyl radicals containing from 1 to 5 carbon atoms and these radicals including a double bond, and
aralkyl radicals in which the alkyl moiety contains from 1 to 5 carbon atoms;
in racemic and enantiomeric forms.

The prior art in this field is illustrated in particular by published European Patent Application No. 0286.495, which ralates to morpholine compounds of the general formula:

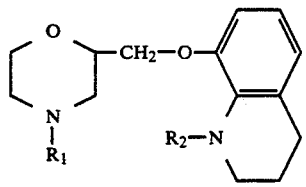

in which $R_1$ and $R_2$ may represent, inter alia, a hydrogen atom or an alkyl radical, but in which the aromatic moiety of the quinoline nucleus is never substituted. The introduction of a substituent x in that aromatic moiety results in the compounds of the present invention, which differ from those of European Application 0286.495 not only in their chemical structure but also in the intensity of their pharmacological effects and in their excellent oral bioavailability. Thus, they exert an antihypoxic activity at a much lower dose than the compounds of the prior art. This protection is exerted by the facilitation of noradrenergic neurotransmission. Unlike the compounds of the prior art, the compounds of the present invention can thus just as much counteract noradrenergic deficiency as enhance the liberation of noradrenaline induced experimentally. This facilitation is exerted at very low doses at which the compounds of the prior art have no effect at all, and is exerted with an oral bioavailability two to three times greater than that of the compounds used as reference products.

The present invention also relates to a process for the preparation of the compounds of the general formula I, characterised in that:

(A) in the case where R' represents a hydrogen atom:
a substituted morpholine of the general formula II:

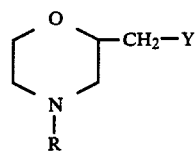

in which:
R is a protecting group, such as a benzyl or trityl group, and
Y is a chlorine or bromine atom or a tosyloxy radical,
is reacted with an alkali metal salt of hydroxyquinoline of the general formula III:

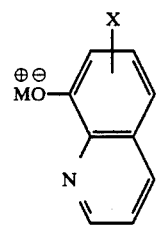

in which
X is as defined hereinbefore and
M is an alkali metal, such as sodium or potassium;
and the compound so-obtained of the general formula IV:

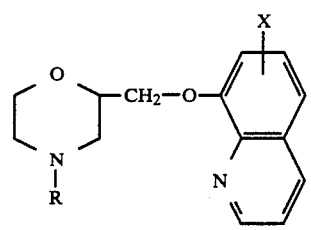

in which R and X are as defined hereinbefore, is reduced, so as to obtain compounds I in which R' is a hydrogen atom, that is to say compounds corresponding more specifically to the general formula I':

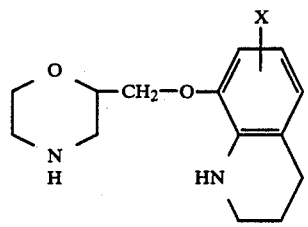

in which X is as defined hereinbefore; and
(B) in the case where R' is selected from the group consisting of:
straight-chain or branched alkyl radicals containing from 1 to 5 carbon atoms and optionally including a double bond, and aralkyl radicals in which the alkyl moiety contains from 1 to 5 carbon atoms:

the compound of formula IV defined hereinbefore is reduced, the reduction being carried out by means of a borohydride, (such as NaBH₃CN) as described hereinbefore;

then the intermediate compound of the general formula V:

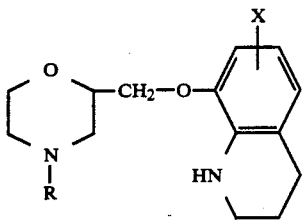

in which X and R are as defined hereinbefore, is alkylated, the alkylation being effected:

either by means of an aldehyde of the formula R"—CHO in which R" is selected from the group consisting of:

a hydrogen atom, straight-chain or branched alkyl radicals containing from 1 to 4 carbon atoms and optionally including a double bond, and aralkyl radicals in which the alkyl moiety contains from 1 to 4 carbon atoms and NaBH₃CN, or by means of an acid of the formula R"COOH in which R" is as defined hereinbefore, and NaBH₄, and finally the resulting compounds of the general formula VI:

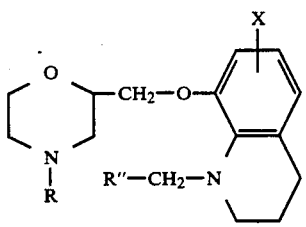

in which X, R and R" are as defined hereinbefore, are debenzylated or detritylated, by proceeding as described hereinbefore (to prepare the compounds I'), so as to obtain compounds I in which R' is selected from the group consisting of:

straight-chain or branched alkyl radicals containing from 1 to 5 carbon atoms and optionally including a double bond, and aralkyl radicals in which the alkyl moiety contains from 1 to 5 carbon atoms, that is to say, compounds corresponding more specifically to the general formula I":

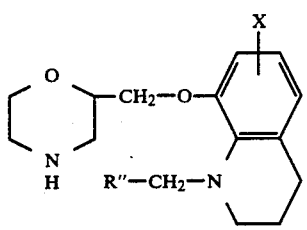

in which X and R" are as defined hereinbefore.

The condensation of compounds II and III is especially advantageously carried out in a polar aprotic solvent, such as, for example, dimethylformamide or dimethylacetamide.

It is also possible to carry out the condensation of compound II with compound III in the form of the sodium or potassium salt by solid-liquid phase transfer in an aprotic solvent, such as an aromatic hydrocarbon, such as, for example, toluene or xylene, in the presence of a quaternary ammonium salt of high molecular weight, such as, for example, Adogen, at a temperature of from 90° to 120° C.

The reduction of compound IV in which R is a benzyl radical is carried out by means of hydrogen at reduced pressure (from 2 to 5 atmospheres) in the presence of a catalyst belonging to the metals of group VIII, such as rhodium or palladium on carbon (the palladium can also be used in hydroxide form) in a polar solvent, such as a low-molecular-weight alcohol, at a temperature of from 20° to 60° C. In this case the benzyl protecting group is removed at the same time.

If it is desired to avoid the use of hydrogen, the reduction of compound IV can be effected by means of a borohydride. The most advantageous method comprises starting from a compound of formula IV in which R represents a trityl radical, so that by hydrolysis by means of a mineral or organic acid it is possible to obtain a compound of formula IV in which R has been replaced by a hydrogen atom, the latter being reduced in a conventional manner by a borohydride, such as NaBH₃CN, in a polar solvent, such as methanol or ethanol, in pure form or in admixture with water, at a pH of from 6 to 7.

The alkylation of compounds V by means of R"—CHO and NaBH₃CN is carried out in a polar aprotic solvent (such as, for example, CH₃CN) in pure form or in admixture with water, at a pH controlled in accordance with the method described by R. BORCH & coll., J. Am. Chem. Soc. 93, 2897 (1971).

The alkylation of compounds V by means of R"COOH and NaBH₄ is carried out in a polar aprotic solvent (such as, for example, tetrahydrofuran or dioxan) according to the method described by GRIBBLE and HEALD, Synthesis (1975), 650.

The compounds of the general formula I yield salts with physiologically tolerable acids, which salts, as such, are included in the present invention.

The compounds of the present invention have valuable pharmacological and therapeutic properties. They counteract in particular cerebral disorders resulting from a reduced supply of oxygen. Their principal mechanism is the facilitation of noradrenergic neurotransmission, neurotransmission which is closely associated with the phenomena of attentiveness, alertness and memory and of which the deficiency in functioning is broadly demonstrated in cerebral pathologies such as cerebral ageing, depression or cerebral vascular accident.

These valuable properties are exerted more intensely and pharmacotoxicologically much more safety by the compounds of the present invention than by the compounds of European Patent Application No. 0286.495 of which the compound of Example 2, R,S-8-[2-morpholinyl)-methoxy]-1,2,3,4-tetrahydroquinoline, was the most active compound, as shown by the pharmacological study described thereinafter in Example 8.

Thus, the compounds of the present invention prove useful for the therapeutic treatment of syndromes associated with reduced oxygenation and a deficiency in noradrenergic neurotransmission, such as cerebral vascular accident or cerebral ageing.

These beneficial effects permit them to protect the neurones and to improve the phenomena of reduction in attentiveness, concentration and alertness as well as conditions of depression and amnesia which always accompany ischaemia and degenerative cerebral disorders as well as ageing.

The present invention also relates to pharmaceutical compositions containing as active ingredient a compound of the general formula I or a physiologically tolerable salt thereof, in admixture or association with an appropriate pharmaceutical excipient, such as, for example, glucose, lactose, starch, talc, ethyl cellulose, magnesium stearate or cocoa butter.

The pharmaceutical compositions so obtained are generally in dosage form and may contain from 0.5 to 100 mg of active ingredient. They may, for example, be in the form of tablets, dragees, gelatin-coated pills, suppositories, injectable or drinkable solutions and, depending on the case in question, may be administered orally, rectally or parenterally at a dose of from 0.5 mg to 100 mg taken 1 to 3 times per day.

The following Examples illustrate the present invention, the melting points being determined with a Kofler hot plate unless specified otherwise.

EXAMPLE 1

R,S-6-fluoro-8-(2-morpholinylmethoxy)-1,2,3,4-tetrahydroquinoline.

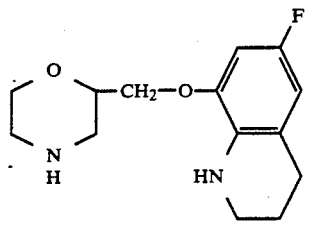

(a) Preparation of:

R,S-6-fluoro-8-(4-benzyl-2-morpholinylmethoxy)-quinoline:

9.54 g of the sodium salt of 6-fluoro-8-hydroxyquinoline, melting at 134° C., 19 g of R,S-2-tosyloxymethyl-4-benzylmorpholine, melting at 74° C., 1.2 g of Adogen 464 and 250 ml of toluene are introduced into a round-bottomed flask provided with a very efficient stirrer and a condenser. The whole is refluxed for 7 hours. Then, an additional 10 g of R,S-2-tosyloxymethyl-4-benzylmorpholine are added and refluxing is continued for a further 16 hours.

After cooling, the whole is filtered and the filtrate is washed 4 times with normal sodium hydroxide solution, dried over sodium sulphate and concentrated to dryness. The residue is chromatographed on 1.6 l of silica (35–70μ). Ethyl acetate is used as eluant. The fractions retained are concentrated to dryness. 11.9 g of gummy residue are obtained. Yield: 65.5%.

The sodium salt of 6-fluoro-8-hydroxyquinoline used as starting material was prepared as follows:

2.06 g of sodium hydroxide in pellet form are dissolved in 2.5 ml of water. 150 ml of methanol and 8.39 g of 6-fluoro-8-hydroxyquinoline are added. The whole is stirred until dissolved, then concentrated to dryness and dried at 50° C. under 0.5 Torr. 9.54 g of the sodium salt of 6-fluoro-8-hydroxyquinoline are obtained in a yield of 100%.

(b) Reduction of:

R,S-6-fluoro-8-(4-benzyl-2-morpholinylmethoxy)-quinoline:

11.2 g of R,S-6-fluoro-8-(4-benzyl-2-morpholinylmethoxy)-quinoline, 400 ml of methanol, 62 ml of N hydrochloric acid and 1.12 g of 10% palladium-on-carbon are introduced into a stainless steel flask. The whole is hydrogenated for 3 hours at 60° C. under a pressure of 6 kg. The palladium is filtered off and replaced by the same quantity of the same catalyst. The whole is again hydrogenated for 3 hours at 60° C. under a pressure of 6 kg. The catalyst is for the last time replaced by the same quantity of the same fresh catalyst and is again hydrogenated for 3 hours at 60° C. under 6 kg. The whole is filtered and the filtrate is concentrated to dryness. The residue is taken up in a 10% solution of sodium carbonate, extracted several times with methylene chloride and dried over sodium sulphate.

The product is concentrated to dryness yielding 7.4 g of residue which is dissolved in 74 ml of ethanol. 2.67 g of methanesulphonic acid are added and crystallisation is observed. The crystals are suctioned off, washed with iced ethanol and dried at 70° C. under 0.5 torr. 8.5 g of the monomethanesulphonate of R,S-6-fluoro-8-(2-morpholinylmethoxy)-1,2,3,4-tetrahydroquinoline, melting at 189° C., are obtained. Yield: 80%.

By operating as described above in Example 1, starting from 6-fluoro-8-hydroxyquinoline and, respectively:

R-2-tosyloxymethyl-4-benzylmorpholine,
  m.p.: 72° C., $[\alpha]_D^{21} = -19.9°$ (c=2, CH$_3$OH), and S-2-tosyloxymethyl-4-benzylmorpholine,
  m.p.: 72° C., $[\alpha]_D^{21} = +21°$ (c=2, CH$_3$OH), the R- and the S-6-fluoro-8-(4-benzyl-2-morpholinylmethoxy)quinoline are obtained which, on hydrogenation, yield, respectively: the R- and the S-6-fluoro-8-(2-morpholinylmethoxy)-1,2,3,4-tetrahydroquinolines with which there are obtained, respectively:

(α) R-6-fluoro-8-(2-morpholinylmethoxy)-1,2,3,4-tetrahydroquinoline monomethanesulphonate, m.p. (cap): 190°–191° C., $[\alpha]_D^{21} = -4.8°$ (c=1, DMSO), and (β) S-6-fluoro-8-(2-morpholinylmethoxy)-1,2,3,4-tetrahydroquinoline monomethanesulphonate, m.p. (cap): 191°–192° C., $[\alpha]_D^{21} = +3.3°$ (c=1, DMSO).

EXAMPLE 2

R,S-5-fluoro-8-(2-morpholinylmethoxy)-1,2,3,4-tetrahydroquinoline:

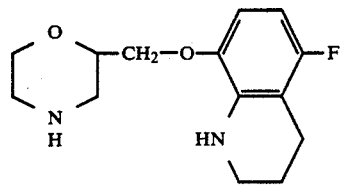

(a) Preparation of:

R,S-5-fluoro-8-(4-trityl-2-morpholinylmethoxy)-quinoline:

8.87 g of the sodium salt of 5-fluoro-8-hydroxyquinoline, melting at 114° C., 27.1 g of R,S-2-tosyloxymethyl- 4-tritylmorpholine, melting at 252° C., 1 g of Adogen 464 and 250 ml of toluene are introduced into a three-necked round-bottomed flask fitted with a stirrer and a very efficient condenser. The whole is refluxed for 20 hours with stirring and is then filtered and concentrated to dryness.

The product is chromatographed on 2.1 l of silica (AMICON - (35–70μ) using a mixture of methylene chloride and ethyl acetate (95:5) as eluant. The fractions retained are concentrated to dryness, taken up in methylene chloride and washed three times with N sodium hydroxide solution in order to remove traces of starting materials.

The whole is dried on sodium sulphate and concentrated to dryness, yielding 16.6 g of R,S-5-fluoro-8-(4-trityl-2-morpholinylmethoxy)-quinoline in the form of a thick gum. Yield: 69%.

The sodium salt of 5-fluoro-8-hydroxyquinoline was prepared by the same method as its 6-fluoro homologue (cf. end of Example 1a).

(b) Preparation of:

R,S-5-fluoro-8-(2-morpholinylmethoxy)-quinoline:
13.74 g of R,S-5-fluoro-8-(4-trityl-2-morpholinylmethoxy)-quinoline prepared above are stirred very thoroughly for 3 hours in 200 ml of normal hydrochloric acid and 250 ml of ether. The aqueous phase is decanted, washed once with ether, rendered alkaline by sodium carbonate in powder form, and extracted with methylene chloride. The organic phase is dried over sodium sulphate and concentrated to dryness. 6.6 g of R,S-5-fluoro-8-(2-morpholinylmethoxy)-quinoline are obtained in the form of a gum. Yield: 92.5%.

(c) Reduction of:

R,S-5-fluoro-8-(2-morpholinylmethoxy)-quinoline:
6.6 g of R,S-5-fluoro-8-(2-morpholinylmethoxy)-quinoline and 250 ml of methanol are introduced into a three-necked round-bottomed flask provided with a stirrer, a thermometer, a condenser and a dropping funnel.

6.3 g of sodium cyanoborohydride are cautiously added. The temperature increases from 20° to 35° C. The mixture is brought to reflux and, over a period of one hour, 100 ml of normal hydrochloric acid are added.

A second alternated introduction of sodium cyanoborohydride and normal hydrochloric acid is then carried out under the same conditions of time, temperature and quantity as before.

Refluxing is maintained for 10 minutes after the end of the second introduction, then the whole is concentrated to dryness. The residue is taken up in a mixture of methylene chloride and 10% aqueous sodium carbonate solution.

The aqueous phase is extracted several times with methylene chloride. The combined organic phases are dried over sodium sulphate and concentrated to dryness. The residue is chromatographed on 500 ml of silica AMICON (35–70 μ) under a pressure of 1 bar, using a mixture of methylene chloride and methanol (80:20) as eluant. The fractions retained are concentrated to dryness.

4.8 g of R,S-5-fluro-8-(2-morpholinylmethoxy)-1,2,3,4-tetrahydroquinoline are obtained in the form of a thick gum. This gum is taken up in 18 ml of hot ethanol. A mixture containing 1.73 g of methanesulphonic acid dissolved in 30 ml of ethanol is added.

Crystallisation is observed. The crystals are suctioned off, washed with iced ethanol and dried at 70° C. under 10 torr.

5.7 g of the monomethanesulphonate of R,S-5-fluoro-8-(2-morpholinylmethoxy)-1,2,3,4-tetrahydroquinoline are obtained, m.p.: 201° C. Yield: 63%.

By proceeding as described above in Example 2a), starting from 5-fluoro-8-hydroxyquinoline and, respectively:
R-2-tosyloxymethyl-4-tritylmorpholine,
  m.p.: 250° C., $[\alpha]_D^{21} = +17°$ (c=1, CHCl$_3$), and
S-2-tosyloxymethyl-4-tritylmorpholine,
  m.p.: 250° C., $[\alpha]_D^{21} = -15.8°$ (c=1, CHCl$_3$),
there are obtained, respectively:
R-5-fluoro-8-(4-trityl-2-morpholinylmethoxy)-quinoline, $[\alpha]_D^{20.5} = +67.9°$ (c=1, CHCl$_3$), and S-5-(fluoro-8-(4-trityl-2-morpholinylmethoxy)-quinoline, $[\alpha]_D^{21} = -68°$ (c=1, CHCl$_3$),
which, treated in accordance with the method described in Example 2b), yield, respectively:
R-5-fluoro-8-(2-morpholinylmethoxy)-quinoline, $[\alpha]_D^{22} = +4.4°$ (c=1, C$_2$H$_5$OH),
and S-5-fluoro-8-(2-morpholinylmethoxy)-quinoline $[\alpha]_D^{21} = -4.7°$ (c=1, C$_2$H$_5$OH),
which by means of reduction yield, respectively:
R- and S-5-fluoro-8-(2-morpholinylmethoxy)-1,2,3,4-tetrahydroquinoline with which there are obtained, respectively:
(α) R-5-fluoro-8-(2-morpholinylmethoxy)-1,2,3,4-tetrahydroquinoline monomethanesulphonate, m.p. (cap: 193°–194° C., $[\alpha]_D^{21} = +4.55°$ (c=1, C$_2$H$_5$OH), and
(β) S-5-fluoro-8-(2-morpholinylmethoxy)-1,2,3,4-tetrahydroquinoline monomethanesulphonate, m.p. (cap): 193°–194° C., $[\alpha]_D^{21} = -4.75°$ (c=1, C$_2$H$_5$OH).

EXAMPLES 3 and 4:

By proceeding in accordance with the method described in Example 2, the following were prepared:
(3) R,S-5-chloro-8-(2-morpholinylmethoxy)-1,2,3,4-tetrahydroquinoline (m.p. of the corresponding monomethanesulphonate: 180° C.), and the corresponding R and S enantiomers, and
(4) R,S-5-trifluoromethyl-8(2-morpholinylmethoxy)-1,2,3,4-tetrahydroquinoline, m.p. (cap): 101°–103° C. m.p. (cap) of the corresponding monomethane sulphonate: 178°–180° C., [starting from 5-trifluoromethyl-8-hydroxy-quinoline, m.p.: 98° C.]. and the corresponding R and S enantiomers

EXAMPLE 5:

R,S-6-fluoro-1-methyl-8-(2-morpholinylmethoxy)-1,2,3,4-tetrahydroquinoline.

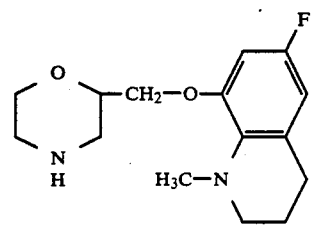

(a) 5.3 ml of 40% Formol and 1.3 g of sodium cyanoboro-hybride followed by 0.66 ml of acetic acid (pH=5) are added to a solution of 4.7 g of 6-fluro-8-(4-benzyl-2-morpholinylmethoxy)-quinoline (prepared according to Example 1a) in 30 ml of acetonitrile.

An increase in temperature is observed: the mixture is cooled to 20° C. and stirred at that temperature for two hours.

The whole is evaporated to dryness, and the residue is taken up in $CH_2Cl_2$ and N NaOH and extracted several times with $CH_2Cl_2$. The solvent is evaporated off and the residue is chromatographed on 2.5 kg of silica (35-70 $\mu$) using a mixture of $CH_2Cl_2$ and acetone (9:1) as eluant. After evaporation of the eluates, 3.7 g of product are recovered in the form of a thick oil.

(b) 3.6 g of R,S-6-fluro-1-methyl-8-(4-benzyl-2-morpholinylmethoxy)-1,2,3,4-tetrahydroquinoline obtained above. are dissolved in 70 ml of ethanol. 20 ml of N HCl are added and the whole is hydrogenated under 6 atmospheres of hydrogen in the presence of 0.5 g of $Pd(OH)_2$ (Pearlman catalyst) at 60° C. At the end of 20 hours the hydrogenolysis is complete. The catalyst is filtered off and the solvent is evaporated. The residue is extracted with $CH_2Cl_2$, washed several times with water, decanted and evaporated. 2.3 g of resinous product is obtained which is converted into the methanesulphonate in ethanol. 2.3 g of the methanesulphonate of R,S-6-fluoro-1-methyl-8-(2-morpholinylmethoxy)-1,2,3,4-tetrahydroquinoline are obtained in this manner.

The corresponding R and S enantiomers were prepared by proceeding in the same manner.

EXAMPLES 6 AND 7:

The following were prepared by proceeding in accordance with the methods described in Example 5:

(6) R,S-5-fluoro-1-methyl-8-(2-morpholinylmethoxy)-1,2,3,4-tetrahydroquinoline [starting from 5-fluoro-8-(4-trityl-2-morpholinylmethoxy)-quinoline prepared according to Example 2a] and the corresponding R and S enantiomers, and (7) R,S-5-trifluoromethyl-1-methyl-8-(2-morpholinylmethoxy)-1,2,3,4-tetrahydroquinoline, the monomethanesulphonate thereof m.p.(cap): 122°-124° C., [starting from 5-trifluoromethyl-8-(4-benzyl-2-morpholinylmethoxy)-quinoline m.p.(cap): 130°-132° C.] and the corresponding R and S enantiomers.

EXAMPLE 8:

Pharmacological study:

The compounds of the present invention were tested by comparison with the most active prior art product, that is R,S-8-[(2-morpholinyl)methoxy]-1,2,3,4-tetrahydroquinoline (Example 2 of European Patent Application No. 0286.495), hereinafter referred to as "the reference product".

1. Cerebral protecting effects in mice:

Male mice are subjected to acute global hypoxia in a barometric depressurization chamber in which the pressure is rapidly lowered to 160 mbar. The cerebral survival time taken as the occurrence of the last respiratory gasp is measured in control animals and in animals that have received the compound under examination 30 minutes beforehand by the intraperitoneal route.

Under these conditions, the compounds of the invention significantly counteract hypoxia and delay cerebral death from a dose of 3 $\mu$mols/kg.

For example, at that dose an increase in the survival time of 18% ($p<0.03$) is observed with the produce of Example 1$\alpha$ and of 21% ($p<0.05$) with the produce of Example 2$\beta$. The same protecting effect with the reference product is not obtained until a dose of 9 $\mu$mols/kg.

When the compounds are administered orally 60 minutes before hypoxia, the produce of Example 1$\alpha$ increases the survival time by 37% at a dose of 9 $\mu$mols/kg whilst the reference produce causes an increase of 31% at a dose of 40 $\mu$mols/kg. The compounds of the present invention thus have an excellent oral bioavailability even at the very low doses examined, since the relationship between the active doses by the p.o. and i.p. routes is between 2 and 3.

The antihypoxic effect of the compounds of the invention is also associated with the dose, as shown, for example, by the following results:

| Products tested | DOSES ($\mu$mols/kg i.p.) | | | |
|---|---|---|---|---|
| | 3 | 9 | 30 | 90 |
| Example 1$\alpha$ | +18% | +37% | +55% | +114% |
| Example 1$\beta$ | +21% | +42% | +62% | +108% |
| Reference product | +5% | +17% | +42% | +87% |

2. Noradrenergic facilitating effects in vivo (a) Lethal dose test with yohimbine in mice Male mice are administered yohimbine ($\alpha$2 antagonist) by the intraperitoneal route at a dose of 30 mg/kg, a non-lethal dose which only causes the occurrence of hyperexcitability symptoms or convulsions. Any compound that facilitates noradrenergic neurotransmission potentiates the releasing effect of the yohimbine and brings about the death of the animals.

A percentage mortality is thus measured for each group of animals treated 30 minutes beforehand i.p. or 60 minutes beforehand p.o. with the compound examined.

Under these conditions the compounds of the present invention exhibit a marked noradrenergic facilitating effect from a dose of 9 $\rho$mols/kg i.p. (mortality=15 to 30%). This effect is identical to that of the reference product (+20%) but the oral bioavailability, expressed by the relationship between the mean effective p.o. and i.p. doses, proves far better in the case of the compounds of the invention. This relationship is, in fact, 4.25 for the reference produce whilst it is only 3.16 for the product of Example 1$\alpha$ and 1.77 for the produce of Example 2$\alpha$.

(b) Hypothermia with apomorphine in mice

The administration of a very strong dose of apomorphine (16 mg/kg i.p.) causes hypothermia of approximately 4° C. by the stimulation of dopaminergic heteroreceptors situated on the noradrenergic neurones. The so-created hypothermia is thus due to the failure of noradrenergic neurotransmission. The facilitating agents administered 30 minutes beforehand counteract this hypothermia.

Under these conditions, the compounds of the invention have an inhibiting effect vis-a-vis hypothermia from a dose of 3 $\mu$mols/kg (product of Example 2$\beta$:—16%; produce of Example 1: —27%) whilst the reference product has no effect. The same applies at a dose of 9 μmols/kg (product of Example 2β:−21%; produce of Example 1:−46%; produce of Example 2:−29%; reference product:+0.5%).

3. Noradrenergic facilitating effect in vitro

This effect was examined in the seahorse by measuring the synaptosomal reuptake of noradrenaline (NAD). For this, a fraction of synaptosomes is placed in the presence of tritiated NAD with or without previous incubation with the compound examined.

A measurement of the radioactivity in the synaptosomal pellet makes it possible to calculate the quantity of NAD reuptaken naturally by neurone endings. A compound inhibiting the reuptake reduces the radioactivity measured and a percentage inhibition is measured by comparison with a control preparation.

At a dose of $10^{-6}M$, the reference produce inhibits the reuptake of NAD by 33.6%. The compounds of the invention counteract this reuptake more intensely (product of Example 1β:−55.4%; product of Example 2β:−58.9%).

4. Psycho-awakening effects in mice

Male mice are administered sodium barbital by the i.p. route at a dose of 270 mg/kg. The duration of the narcosis so induced is compared between control animals and animals treated beforehand by the i.p. route with the compounds examined.

At a dose of 30 μmols/kg, the reference product significantly counteracts narcosis with barbital (−20%, p<0.05). Under the same conditions and at the same dose, the compounds of the invention have a marked effect (product of Example 2β:40%, p<0.02; product of Example 1:−36%, p<0.01).

This antagonism of barbital-induced narcosis reflects a psycho-awakening effect since no antagonism occurs when narcosis is induced with hexobarbital (75 mg/kg i.p.) (product of Example 2β:+20%; product of Example 1:+26%).

We claim:

1. A compound selected from the group consisting of: morpholine compounds of the general formula (I):

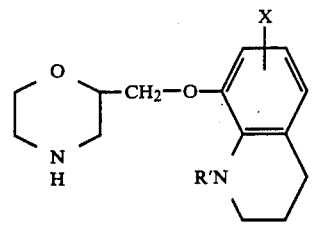

in which
X, bonded to the aromatic nucleus, is selected from the group consisting of:
a halogen atom and
a trifluoromethyl radical; and
R' is selected from the group consisting of:
a hydrogen atom,
a straight-chain or branched alkyl radical containing 1 to 5 carbon atoms and such radical including a double bond, and
an aralkyl radical in which the alkyl moiety contains 1 to 5 carbon atoms;
in racemic and enantiomeric forms; and physiologically tolerable salts thereof with appropriate acids.

2. A compound of claim 1 which is selected from: R,S-6-fluoro-8-(2-morpholinylmethoxy)-1,2,3,4-tetrahydroquinoline and its enantiomers and salts thereof.

3. A compound of claim 1 which is selected from: R,S-5-fluoro-8-(2-morpholinylmethoxy)-1,2,3,4-tetrahydroquinoline and its enantiomers and salts thereof.

4. A compound of claim 1 which is selected from: R,S-5-chloro-8-(2-morpholinylmethoxy)-1,2,3,4-tetrahydroquinoline and its enantiomers and salts thereof.

5. A compound of claim 1 which is selected from: R,S-5-trifluoromethyl-8-(2-morpholinylmethoxy)-1,2,3,4-tetrahydroquinoline and its enantiomers and salts thereof.

6. A compound of claim 1 which is selected from: R,S-6-fluoro-1-methyl-8-(2-morpholinylmethoxy)-1,2,3,4-tetrahydroquinoline and its enantiomers and salts thereof.

7. A compound of claim 1 which is selected from: R,S-5-fluoro-1-methyl-8-(2-morpholinylmethoxy)-1,2,3,4-tetrahydroquinoline and its enantiomers and salts thereof.

8. A compound of claim 1 which is selected from: R,S-5-trifluoromethyl-1-methyl-8-(2-morpholinylmethoxy)-1,2,3,4-tetrahydroquinoline and its enantiomers and salts thereof.

9. A pharmaceutical composition useful against ischaemic syndromes or cerebral aging containing as active ingredient an effective amount of a compound according to claim 1 together with pharmaceutically-acceptable excipient.

10. A method for treating a living animal body afflicted with an ischaemic syndrome or cerebral aging comprising the step of administering to the said living animal body an amount of a compound of claim 1 which is effective for the alleviation of the said condition.

* * * * *

UNITED STATES PATENT AND TRADEMARK OFFICE
CERTIFICATE OF CORRECTION

PATENT NO. : 5,026,701

DATED : Jun. 25, 1991

INVENTOR(S) : Gilbert Regnier, Claude Guillonneau, Jean Lepagnol, Pierre Lestage It is certified that error appears in the above-identified patent and that said Letters Patent is hereby corrected as shown below:

```
Column 4,  line 60;  "safety" should read -- safely --.
Column 10, line 5;   "produce" should read -- product --.
Column 10, line 6;   "produce" should read -- product --.
Column 10, line 10;  "produce" should read -- product --.
Column 10, line 12;  "produce" should read -- product --.
Column 10, line 46;  "ρmols/kg" should read -- μmols/kg --.
Column 10, line 52;  "produce" should read -- product --.
Column 10, line 53;  "produce" should read -- product --.
Column 10, line 68;  "produce" should read -- product --.
Column 11, line 5;   "produce" should read -- product --.
Column 11, line 5;   "produce" second occurrence, should read -- product --.
Column 11, approximately line 26; "produce" should read -- product --.
```

Signed and Sealed this

Third Day of November, 1992

Attest:

DOUGLAS B. COMER

*Attesting Officer*         *Acting Commissioner of Patents and Trademarks*